United States Patent
Hofmann et al.

(10) Patent No.: US 8,418,868 B2
(45) Date of Patent: Apr. 16, 2013

(54) FLUID-COLLECTING CONTAINER

(75) Inventors: Adrian Hofmann, Lucerne (CH); David Imboden, Horgen (CH)

(73) Assignee: Medela Holding AG, Baar (CH)

( * ) Notice: Subject to any disclaimer, the term of this patent is extended or adjusted under 35 U.S.C. 154(b) by 205 days.

(21) Appl. No.: 12/997,935

(22) PCT Filed: Jul. 14, 2009

(86) PCT No.: PCT/CH2009/000250
§ 371 (c)(1), (2), (4) Date: Dec. 14, 2010

(87) PCT Pub. No.: WO2010/006458
PCT Pub. Date: Jan. 21, 2010

(65) Prior Publication Data
US 2011/0163091 A1    Jul. 7, 2011

(30) Foreign Application Priority Data
Jul. 15, 2008    (CH) .................................... 1098/08

(51) Int. Cl.
*B65D 6/28*    (2006.01)

(52) U.S. Cl.
USPC ....... 220/4.01; 220/23.86; 220/501; 220/503; 220/505; 220/524

(58) Field of Classification Search ............... 220/23.83, 220/23.86, 500, 501, 503, 505, 523, 524
See application file for complete search history.

(56) References Cited

U.S. PATENT DOCUMENTS 3,843,016 A * 10/1974 Bornhorst et al. ............ 220/782
4,386,930 A    6/1983 Cianci
(Continued)

FOREIGN PATENT DOCUMENTS

| DE | 19836497 | 2/2000 |
| EP | 0144105 | 6/1985 |

(Continued)

OTHER PUBLICATIONS

International Search Report for corresponding PCT Patent Application No. PCT/CH2009/000250, dated Jan. 18, 2010.

*Primary Examiner* — Mickey Yu
*Assistant Examiner* — Kareen Rush
(74) *Attorney, Agent, or Firm* — McDonnell Boehnen Hulbert & Berghoff LLP

(57) ABSTRACT

A fluid-collecting container for receiving a siphoned-off fluid has a closed chamber for a solidifying agent. The chamber can be opened towards an internal space in the fluid-collecting container under external application of force. At least part of the chamber projects into the internal space in the fluid-collecting container. On the outer side of the container, the chamber is closed by an outer wall which can be pressed inwards, and the chamber is open towards the internal space in the fluid-collecting container by the outer wall being pressed in. The internal space continues to be closed to the outside in the region by the outer wall. The fluid-collecting container has a first and a second housing part which together form the internal space in the fluid-collecting container. The outer wall is formed integrally with a wall of the first housing part, the wall surrounding the outer wall. The fluid-collecting container can be produced cost-effectively and prevents damage to the chamber containing the solidifying agent prior to the use thereof. Furthermore, the chamber can be opened in a simple and safe manner when required.

14 Claims, 4 Drawing Sheets

U.S. PATENT DOCUMENTS

| | | | |
|---|---|---|---|
| 5,103,878 A * | 4/1992 | Cassia | 141/65 |
| 5,225,158 A | 7/1993 | Tayebi et al. | |
| 5,306,430 A * | 4/1994 | Dixon et al. | 210/712 |
| 5,589,145 A | 12/1996 | Kaufman | |
| 2007/0095828 A1* | 5/2007 | Schapiro | 220/23.83 |
| 2007/0185366 A1 | 8/2007 | Masuda et al. | |
| 2008/0230546 A1* | 9/2008 | Cocchiarella | 220/500 |
| 2011/0309075 A1* | 12/2011 | Roth et al. | 220/23.83 |

FOREIGN PATENT DOCUMENTS

| | | |
|---|---|---|
| EP | 0390094 | 10/1990 |
| EP | 0668084 | 8/1995 |
| EP | 0839539 | 5/1998 |
| EP | 1642603 | 4/2006 |
| EP | 1421014 | 12/2010 |
| JP | 05-329471 | 12/1993 |
| JP | 7060231 | 3/1995 |
| JP | 7303875 | 11/1995 |
| JP | 2003-275257 | 9/2003 |
| WO | 2007/043088 | 4/2007 |
| WO | 2007/074497 | 7/2007 |
| WO | 2007/096930 | 8/2007 |
| WO | 2007/128156 | 11/2007 |

* cited by examiner

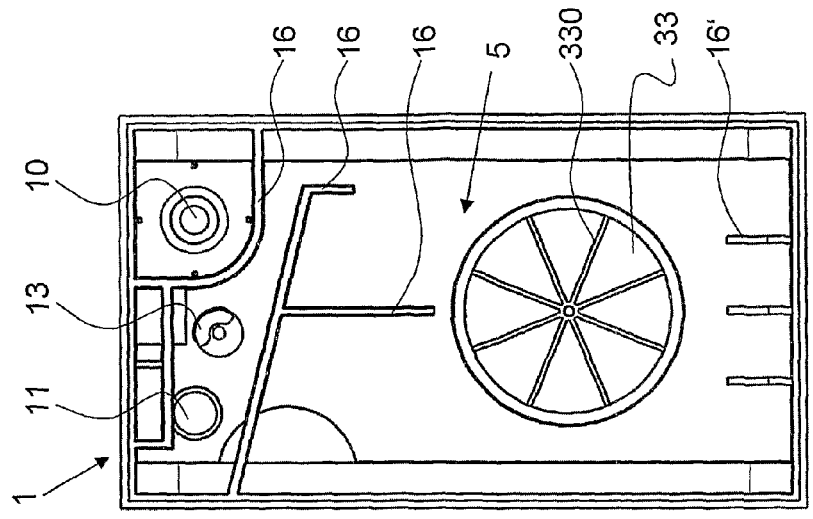
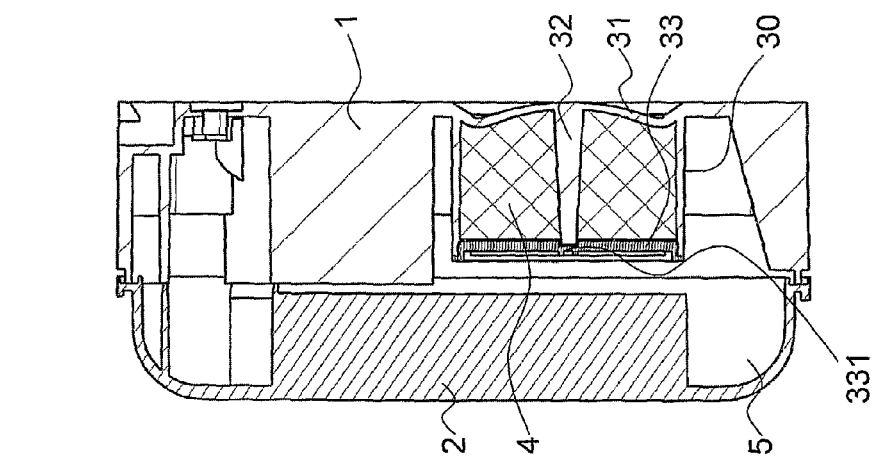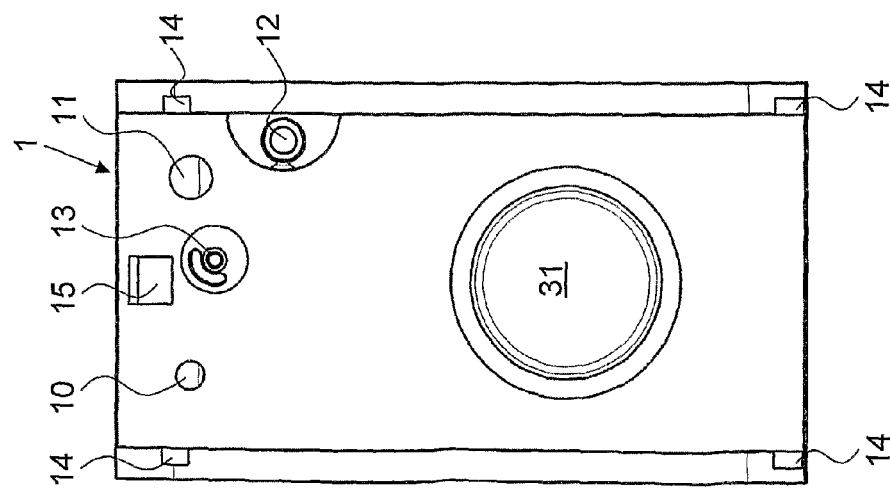

FLUID-COLLECTING CONTAINER

CROSS REFERENCE TO RELATED APPLICATIONS

The present application is a U.S. National Phase Application pursuant to 35 U.S.C. §371 of International Application No. PCT/CH09/00250 filed Jul. 14, 2009, which claims priority to Switzerland Patent Application No. 01098/08 filed on Jul. 15, 2008. The entire disclosure content of these applications are herewith incorporated by reference into the present application.

TECHNICAL FIELD

The invention relates to a fluid-collecting container for receiving an aspirated fluid.

BACKGROUND

Stationary or mobile suction systems are used in the medical field to aspirate body fluids or secretions from body cavities or wounds, particularly in thorax drainage. These systems in each case comprise a suction source, for example a vacuum pump or a central vacuum, and one or more drainage containers. A vacuum line connects the drainage container to the suction source, and a drainage line leads from the drainage container to the patient. The applied vacuum generates an underpressure in the container, and the liquid that is to be aspirated, or the secretion that is to be aspirated, is aspirated from the patient into the drainage container and collected there. The drainage container can be rigid or designed as a flexible bag. The bag can in turn be arranged in a rigid outer container that can be closed in an airtight manner.

A container filled with aspirated body fluid, in particular blood, or with secretion has to be disposed of in the correct way. However, during transport and disposal of the container, there is a danger of fluid escaping, for example if the container was not closed sufficiently tightly. In order to minimize the risk of infection, it is therefore known, in the prior art, to already solidify the collected fluid in the container. Solidifying agents for this are disclosed, for example, in EP-A-0 839 539 and US 2007/0185366.

Various devices are known for introducing these solidifying agents into the container only at the time of use. For example, EP-A-0 668 084 discloses a drainage device with a rigid outer container, and with a flexible inner bag mounted on a lid that closes the outer container. A vacuum connection for connecting to a suction source and a drainage connection for connecting to a patient hose are present in the lid. Arranged on the drainage connection, facing toward the inside of the bag, there is a container that holds a solidifying and disinfecting agent. The container is opened automatically when the vacuum is applied.

EP-A-1 642 603 describes a drainage bag with a container arranged therein for a coagulating agent. The container is soluble in water and dissolves upon contact with an aspirated body fluid, such that the coagulating agent is released into the drainage bag.

JP 5329471 discloses a drainage container with a lid, wherein a suction connection and vacuum connection are present in the lid. A chamber filled with a solidifying agent is additionally present in the lid. The solidifying agent can be conveyed out of the chamber into the drainage container by means of a ram, in order thereby to bind the body fluid aspirated into the container.

JP 7060231 also discloses a drainage container with lid and with a chamber mounted thereon, wherein the chamber in turn contains a solidifying agent. A plug closes an opening of the chamber leading into the drainage container. This plug can be pressed downward by a lever that can be actuated from the outside, such that the opening is freed and the solidifying agent can pass into the drainage container.

JP 7303875 likewise discloses a chamber mounted on a drainage container and holding a thickening agent, the chamber being able to be opened via a relatively complicated mechanism that can be actuated manually from the outside.

These known devices are of relatively complicated construction and are accordingly expensive to produce. The chambers mounted on the outside also have the disadvantage that they get in the way during storage and transport of the container and can also be easily damaged.

SUMMARY

It is therefore an object of the invention to make available a fluid-collecting container which has a chamber for a solidifying agent and which eliminates the abovementioned disadvantages.

The drainage container according to the invention for receiving an aspirated fluid has a closed chamber for a solidifying agent, wherein the chamber can be opened toward an internal space in the fluid-collecting container by application of external force. The chamber protrudes at least partially into the internal space in the fluid-collecting container. The chamber is closed on the outer face of the container by an outer wall that can be pressed inward, wherein the chamber opens toward the internal space in the fluid-collecting container when the outer wall is pressed in, wherein the internal space in this area remains closed off from the outside by the outer wall. The fluid-collecting container has a first and a second housing part which together form the internal space in the fluid-collecting container. The outer wall is formed in one piece with a surrounding wall of the first housing part.

This outer wall that can be pressed in thus forms a tight barrier to the outside, both before and also after the chamber is opened, such that no fluid and also no thickened material can escape to the outside from this area of the internal space. In this area, the chamber also preferably remains closed by this outer wall.

Although the internal space is described here as being closed, its other areas can nevertheless have openings to the outside, for example for the vacuum and drainage connections. Here, "this area" means the area formed by the outer wall that can be pressed in.

In a first embodiment, the outer wall can be pushed toward the internal space, in which case it still has an at least leaktight connection to the rest of the wall of the drainage container. However, it preferably remains stable in position at its edges, and only its inner area can move inward. It is preferably flexible.

In a simple embodiment, by pressing the outer wall inward, the pressure in the chamber is increased such that weak points in its wall directed toward the internal space of the container are broken, as a result of which the solidifying agent can pass into the internal space. However, in a preferred embodiment, at least one transmission member is present and transmits the movement of the outer wall to at least one inner wall of the chamber in order to open the chamber. The transmission member is preferably at least one ram that acts on a lid of the chamber, which lid lies opposite the outer wall and is at least partially removable. A ram is preferably connected to the outer wall or to the lid, preferably being formed in one piece with the wall or the lid. It is preferably arranged centrally in the chamber. The movement of the outer wall needed for opening can be minimized if the ram extends along approximately or exactly the entire length of the chamber.

The ram can be arranged centrally. However, it can also be arranged peripherally or at another suitable position. Instead of a pin-like ram, it is also possible to use a hollow cylindrical ram or a ram with another basic shape. The ram can be hollow or filled with material. It is also possible to use several rams. For example, as an alternative to or in addition to a central ram, several rams can be arranged at uniform intervals and in a circle shape around a central axis of the chamber. Moreover, the rams can have identical or different lengths.

The movable wall is preferably arranged in an outside wall of the collecting container, preferably being arranged in a recessed position therein. If the chamber is recessed in the collecting container, it is better protected during transport and storage.

Since the chamber is an integral part of the internal space, and since the outer wall that can be pressed in is connected in one piece to said surrounding wall of the fluid-collecting container, production is made easier. This additionally ensures that, except for drainage and vacuum connections and any pressure relief valves, the internal space is airtight and leaktight. These advantages are accentuated further if the chamber has a jacket which protrudes into the internal space in the fluid-collecting container and which is formed in one piece with the wall of the fluid-collecting container surrounding the chamber. The same applies if the fluid-collecting container, preferably including the chamber, is made of plastic, for example of polypropylene (PP).

The chamber can be configured in different shapes. For example, it can be spherical, oval or cuboid. However, it is preferably cylindrical and the outer wall is preferably circular.

Further advantageous embodiments are set forth in the dependent claims.

BRIEF DESCRIPTION OF THE FIGURES

The subject matter of the invention is explained below on the basis of a preferred illustrative embodiment which is depicted in the attached drawings, in which:

FIG. 4 shows a first side view of the first part of the fluid-collecting container;

FIG. 5 shows a longitudinal section through the fluid-collecting container;

FIG. 6 shows a second side view of the first part of the fluid-collecting container.

DETAILED DESCRIPTION

Figure 1:
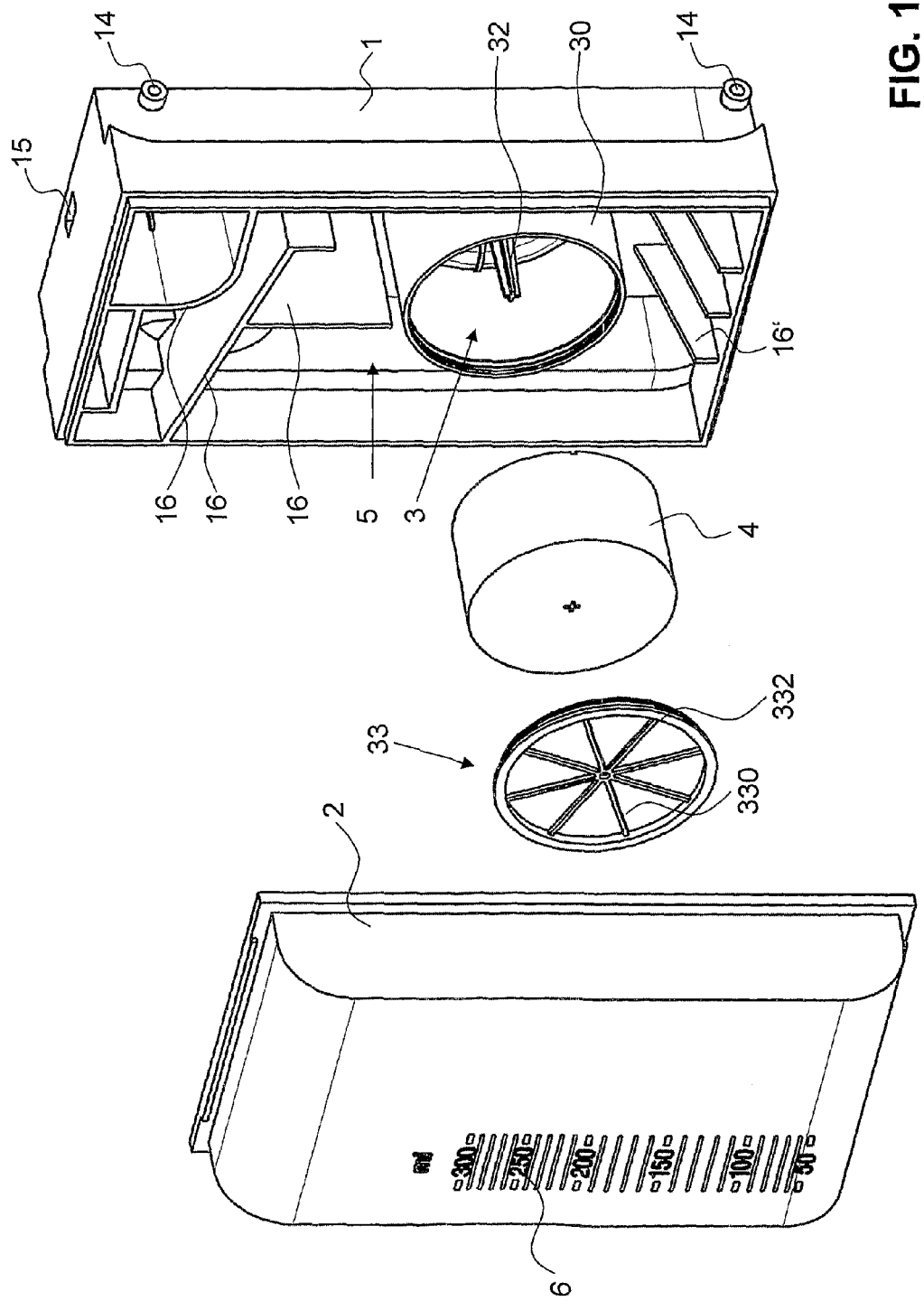
FIG. 1 shows an exploded view of the fluid-collecting container according to the invention.

FIG. 1 shows a drainage or fluid-collecting container according to the invention. Like the containers described at the outset, the container is used in the medical field for receiving aspirated body fluids, for example water, blood or fat. The aspiration takes place in particular during or after surgery or during treatment of disease. An important use is in thorax drainage.

The fluid-collecting container shown has a first container part 1 and a second container part 2. The two container parts 1, 2 are connected to each other in a leaktight and airtight manner. They are preferably plugged together and adhesively bonded or welded to each other. The two container parts 1, 2 form a common internal space, the secretion chamber 5. In the example shown here, other chambers are also present, which are separated by ribs 16 from the secretion chamber but are connected to the latter via channels. Further ribs 16' can also be arranged in the secretion chamber 5 to reduce sloshing movements of the aspirated fluid inside the secretion chamber. This can be seen particularly clearly in FIGS. 3 and 6.

The fluid-collecting container also has a chamber 3 for a solidifying agent 4. This chamber 3 is described in more detail below.

The fluid-collecting container, in this case the second housing part 2, preferably has at least one level indicator 6. This level indicator 6 is nonlinear and takes account of the space occupied in the secretion chamber 5 by the chamber 3.

Figure 2:
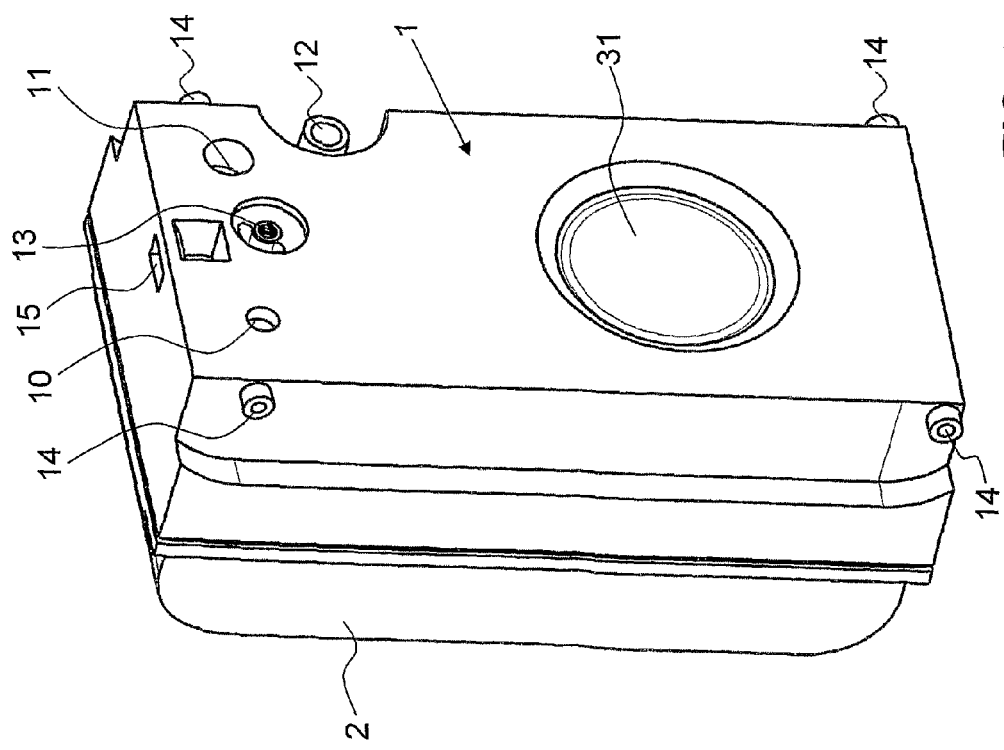
FIG. 2 shows a perspective view of the fluid-collecting container according to FIG. 1.

FIG. 2 shows the container in the assembled state. It can be attached to a suction source, in particular a vacuum pump, via a laterally protruding securing stub 14. A recess 15 serves to receive a locking button of the vacuum pump. In the first housing part 1 there are through-openings leading into the interior of the container. The through-openings form a vacuum connection 10 and a drainage connection 11. The vacuum connection serves for connection to the vacuum pump, either via a direct internal line, as in this example, or via a vacuum tube. The drainage connection 11 serves for connection to a drainage tube, which leads to the cavity from which fluid is to be aspirated from the patient. Depending on the type of suction source, this connection too can be made directly by plugging the drainage tube into this drainage connection 11 or, as in this example, via a connection to the housing of the vacuum pump. The container can preferably have one or more pressure relief valves 13 which open when there is an overpressure in the secretion chamber 5.

As is shown in FIG. 4, the first or second housing part 1, 2 can also have a closure part 12, in particular a stub, for closing the drainage connection. It can be removed from the housing part when necessary.

The two housing parts 1, 2 are preferably made of plastic, preferably polypropylene (PP). Each of the housing parts is preferably made in one piece, the removable closure part 12 being applied by injected molding.

According to the invention, the closed chamber 3 is arranged in the internal space of the container and protrudes at least partially, preferably completely, into this internal space. The chamber 3 is cylindrical in this example and has a hollow cylindrical jacket 30, which protrudes from a rear wall of the first container part 1 into the secretion chamber 5. A first end of the jacket 30 is closed by an outer wall 31. A second, opposite end of the jacket 30 is closed by a lid 33. A ram 32 is arranged centrally on the outer wall 31, the ram 32 extends as far as the lid 33 and is preferably arranged in a socket 331 thereof.

Figure 7:
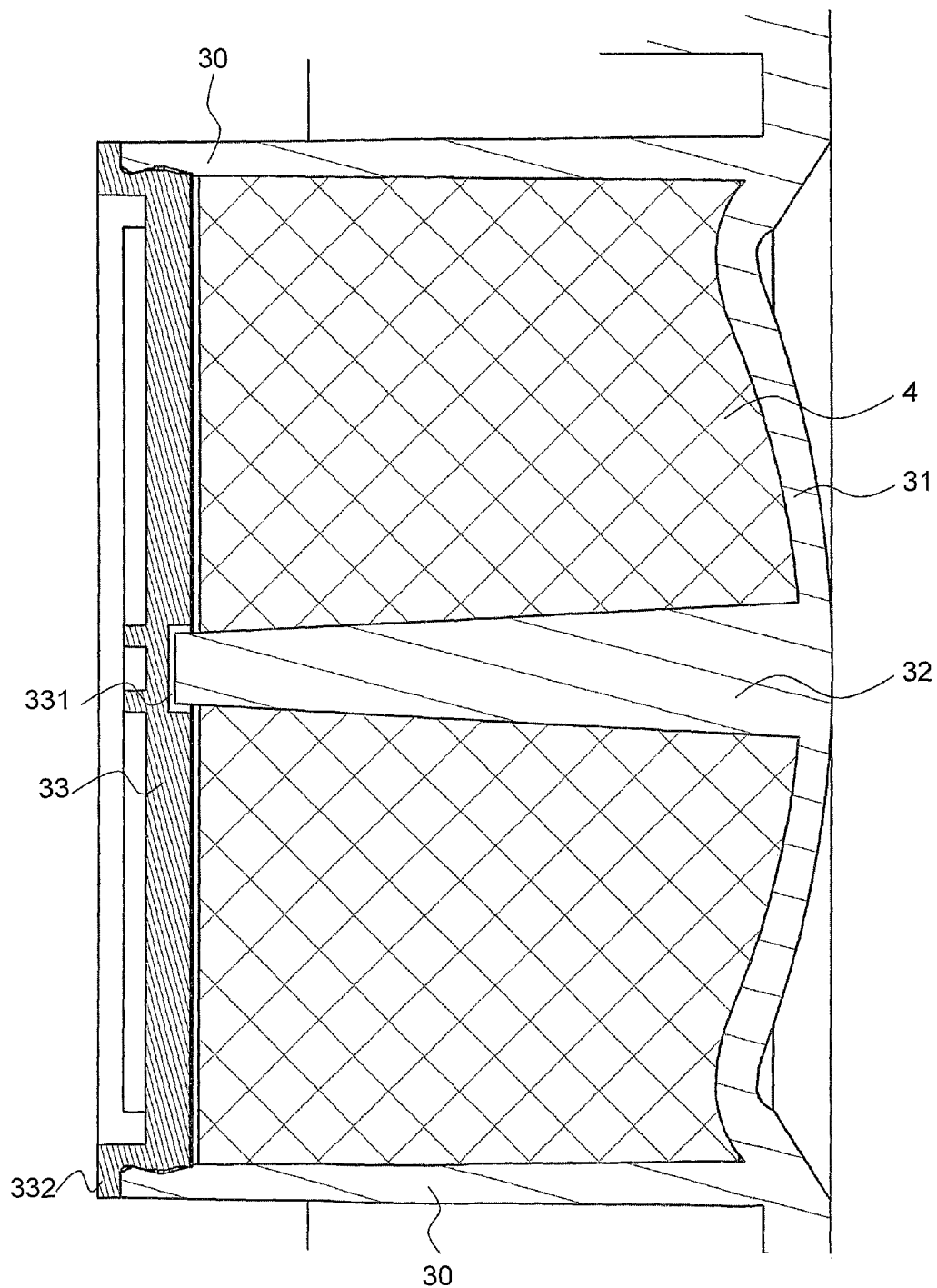
FIG. 7 shows a longitudinal section through a chamber of the fluid-collecting container in an enlarged view.

The jacket 30, the outer wall 31 and the ram 32 are preferably in one piece with the surrounding wall of the first housing part 1, preferably in one piece with the whole of the rest of the housing part 1. This can be seen particularly in FIGS. 5 and 7. The outer wall 31 is preferably flexible or at least is softer than the surrounding area of the rest of the housing part 1. It is preferably connected to this surrounding area via a hinge-like or at least thinned connection, such that it is able to move relative to this area, being able in particular to be pressed in toward the internal space. This direction is preferably parallel to the longitudinal direction of the ram 32 and perpendicular to the surface of the lid 33.

The wall thickness of the entire outer wall 31 is preferably thinner compared to the rest of the area of the housing part 1 surrounding it. It is preferably many times thinner than this remaining area. However, it is also possible for only the hinge or the transition area to be made thinner and therefore softer. In this case, however, it should be ensured, by suitable choice of shape and/or material, that the outer wall 31, when pressed in, is not damaged in such a way that it no longer closes the chamber 3 or the secretion chamber 4 in a leaktight manner.

The outer wall 31 is curved outward here, its outermost point lying flush with the rest of the wall of the first housing part 1. However, this point can also protrude farther outward or be arranged recessed in the rest of the wall.

Figure 3:
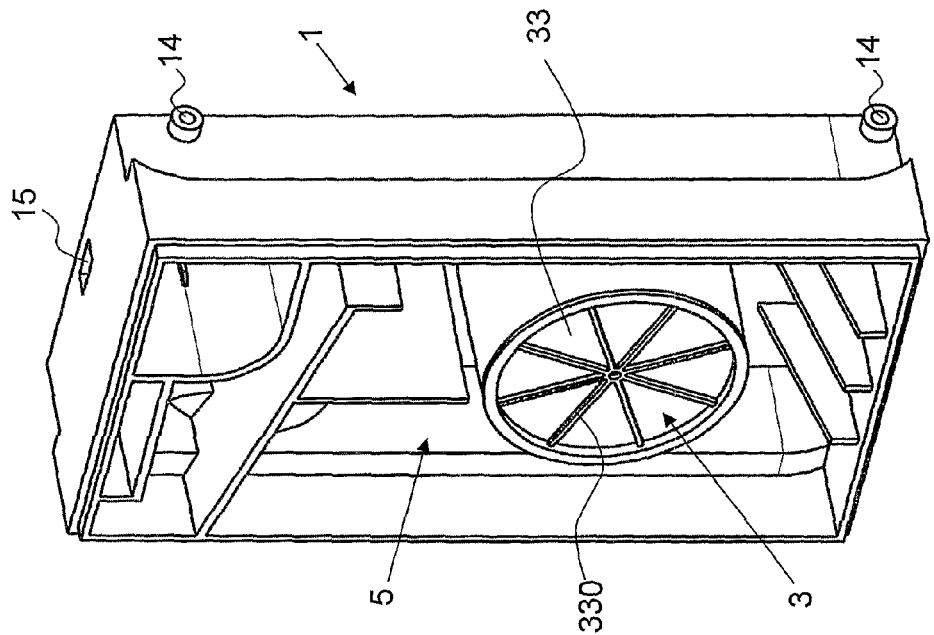
FIG. 3 shows a perspective view of the internal space of a first part of the fluid-collecting container.

The lid 33 is preferably flat. It can preferably be mounted on the jacket 30 with a form fit, and preferably also with a force fit by means of suitable dimensioning (underdimensioning), in which case a peripheral and radially protruding flange 332 serves as abutment. A tight seal is desired but not absolutely necessary. The lid 33 preferably has radially extending ribs 330, as is shown in FIGS. 1, 3 and 6.

The chamber 3 can have a single space, as in the example shown here, or can be divided into several spaces. Moreover, more than one ram 32 can be present. The chamber 3 is preferably arranged in an area at a distance from the drainage and/or vacuum connection 10, 11. In this example, it is arranged in the lower area of the container.

The chamber 3 is used to receive a solidifying agent 4. In FIG. 1, the solidifying agent 4 is shown with a cylindrical shape. This is only a schematic illustration. The solidifying agent is normally a powder or a gel. When the solidifying agent comes into contact or is mixed with the aspirated body fluid, it can cause the latter to form a gel, it can thicken it, form flocks from it or in some other way solidify it. In particular, a gelling agent is used that coagulates the body fluid. Such solidifying agents are well known in the prior art, and some examples, not exhausting the list of possible agents, were mentioned at the outset.

The device described above can now be used as follows according to the invention:

During transport and storage of the fluid-collecting container, i.e. before the latter is used, the solidifying agent 4 is located in the closed chamber 3. During use, the chamber 3 can be opened under the effect of an external force, and the solidifying agent 4 passes into the secretion chamber 5. This can happen just shortly before or during the aspiration of the body fluid. However, this is preferably done after the aspiration has been completed. Depending on the way in which the container is secured, this can take place before or after its removal from the aspiration device.

The chamber 3 is opened by pressing on the outer wall 31 with a hand or a suitable object, but without destroying said outer wall 31. The force applied to the wall 31 is transmitted to the ram 32, which then presses on the lid 33 and pushes the latter away from the jacket 30. The chamber 3 is opened and the solidifying agent 4 can pass into the internal space. In doing this, the chamber 3 and therefore also the secretion chamber 5 remain closed off from the outside in an airtight and leaktight manner as before.

The radial ribs 330 ensure that the pressure applied to the lid 33 is distributed uniformly to the edge of the lid 33, such that the latter, in this example, disengages completely from the jacket. By a suitable choice of the shape of the lid and of the position and number of the rams, it is also possible for the lid to be only partially removed. In particular, it can be secured at one side on the jacket. For example, it can be injection molded in one piece on the jacket via a hinge.

It is also possible for the lid to be provided with holes. For this purpose, it can already have predetermined break points or can be perforated. For this purpose, the ram can be provided with one or more tips. Moreover, instead of the lid, it is also possible for the jacket to be provided with predetermined break points to be perforated, if the outer wall is connected to a suitably shaped force transmission member.

The figures described above show only a preferred example of a fluid-collecting container according to the invention, as can be used for instance in a medical drainage device as per WO 2007/128156. However, the teaching according to the invention is not limited to rigid fluid-collecting containers of this type. In particular, the drainage container can also be formed by a flexible bag. If the bag is connected to a rigid lid for closing a rigid outer container, the chamber can be applied to or integrally formed on the lid. If no rigid lid is present, the chamber can also be arranged on the bag itself, in which case an additional and, if appropriate, removable cover is preferably provided in order to protect the outer wall of the chamber from being pressed in.

The fluid-collecting container according to the invention is inexpensive to produce and prevents damage to the chamber for the solidifying agent prior to use. Moreover, when so required, the chamber can be opened in a simple and reliable way.

The invention claimed is:

1. A fluid-collecting container for receiving an aspirated fluid, wherein the fluid-collecting container has a vacuum connection for connection to a vacuum pump, a drainage connection for connection to a drainage tube, and a closed chamber for a solidifying agent, wherein the chamber can be opened toward an internal space in the fluid-collecting container by application of external force, wherein the chamber protrudes at least partially into the internal space in the fluid-collecting container, and wherein the chamber is closed on an outer face of the container by an outer wall that can be pressed inward, the outer wall defining an area, wherein the chamber opens toward the internal space in the fluid-collecting container when the outer wall is pressed in, wherein the internal space in said area remains closed off from the outside by the outer wall, wherein the fluid-collecting container has a first and a second housing part which form the internal space in the fluid-collecting container, wherein the outer wall is formed in one piece with a surrounding wall of the first housing part, and wherein the chamber comprises a jacket which protrudes from the surrounding wall into the internal space, and wherein the chamber is arranged at a distance from the drainage connection and the vacuum connection.

2. The fluid-collecting container as claimed in claim 1, wherein the outer wall is flexible.

3. The fluid-collecting container as claimed in claim 1, wherein at least one transmission member is present in the chamber and transmits the movement of the outer wall to at least one inner wall of the chamber in order to open the chamber.

4. The fluid-collecting container as claimed in claim 3, wherein the at least one transmission member is a ram acting on a lid of the chamber, the lid being located opposite the outer wall and being at least partially removable.

5. The fluid-collecting container as claimed in claim 4, wherein the at least one ram is connected to the outer wall or to the lid, and is formed in one piece with the wall or the lid.

6. The fluid-collecting container as claimed in claim 1, wherein the outer wall is arranged in an outside wall of the collecting container.

7. The fluid-collecting container as claimed in claim 1, wherein each of the two housing parts is designed in one piece.

8. The fluid-collecting container as claimed claim 1, wherein the chamber has a jacket which protrudes into the internal space in the fluid-collecting container and which is formed in one piece with the surrounding wall of the fluid-collecting container.

9. The fluid-collecting container as claimed in claim 1, wherein the container is made of plastic, including the chamber.

10. The fluid-collecting container as claimed in claim 1, wherein the chamber is cylindrical and the outer wall is circular.

11. The fluid-collecting container as claimed in claim 1, wherein the internal space is a secretion chamber for receiving the aspirated fluid.

12. The fluid-collecting container as claimed in claim 1, wherein the first housing part forms a rear part of the container and comprises a rear wall and wherein the rear wall forms said surrounding wall and wherein the jacket protrudes from said rear wall.

13. The fluid-collecting container as claimed in claim 1, wherein the first housing part forms a rear part of the container and the second housing part forms a front part of the housing.

14. The fluid-collecting container as claimed in claim 1, wherein the chamber is arranged at a distance below the drainage connection and the vacuum connection.

* * * * *